United States Patent
Wang et al.

(10) Patent No.: US 12,077,797 B2
(45) Date of Patent: Sep. 3, 2024

(54) OLIGOPEPTIDE WITH LIPID-LOWERING ACTIVITY, PREPARATION METHOD AND APPLICATION THEREOF

(71) Applicants: Nanjing University of Finance and Economics, Nanjing (CN); Nanjing University of Chinese Medicine, Nanjing (CN)

(72) Inventors: Fang Wang, Anqing (CN); Xinchun Shen, Nanjing (CN); Yong Fang, Nanjing (CN); Zebin Weng, Nanjing (CN)

(73) Assignees: NANJING UNIVERSITY OF FINANCE AND ECONOMICS, Nanjing (CN); NANJING UNIVERSITY OF CHINESE MEDICINE, Nanjing (CN)

( * ) Notice: Subject to any disclaimer, the term of this patent is extended or adjusted under 35 U.S.C. 154(b) by 0 days.

(21) Appl. No.: 18/461,604

(22) Filed: Sep. 6, 2023

(65) Prior Publication Data
US 2024/0084357 A1    Mar. 14, 2024

(30) Foreign Application Priority Data
Sep. 7, 2022    (CN) .......................... 202211092181.6

(51) Int. Cl.
*C07K 1/34*    (2006.01)
*C12P 21/02*    (2006.01)
*C12P 21/06*    (2006.01)

(52) U.S. Cl.
CPC ................ *C12P 21/02* (2013.01); *C07K 1/34* (2013.01)

(58) Field of Classification Search
CPC .. C07K 1/34; C07K 5/10; C12P 21/02; A61K 2300/00; A61K 2800/40
See application file for complete search history.

(56) References Cited

U.S. PATENT DOCUMENTS 11,590,197 B2*    2/2023   Pellecchia .............. A61K 38/05

OTHER PUBLICATIONS

Nanjing University of Chinese Medicine and Nanjing University of Finance and Economics (Applicants), Supplemental Amendment to CN202211092181.6, w/ (allowed) replacement claims, Nov. 13, 2023, Chinese.
CNIPA, Notification to grant patent right for invention in CN202211092181.6, Nov. 20, 2023, Chinese.

* cited by examiner

*Primary Examiner* — Maryam Monshipouri
(74) *Attorney, Agent, or Firm* — Zhigang Ma

(57) ABSTRACT

An oligopeptide with lipid-lowering activity, a preparation method and an application thereof are provided, belonging to the field of biotechnology. The amino acid sequence of the oligopeptide with lipid-lowering activity is shown in SEQ ID NO: 1. The preparation method includes the following steps: (1) hydrolyzing a loach protein with proteases to obtain an enzymatic hydrolysis product; (2) separating the enzymatic hydrolysis product using an ultrafiltration membrane, and taking a component with a molecular weight less than 3 kilodalton (kDa); and (3) filtering and separating the component with the molecular weight less than 3 kDa by Sephadex G-15 to obtain the oligopeptide. The oligopeptide is derived from the loach protein and has the characteristics of high safety, high efficiency, and wide sources.

2 Claims, 8 Drawing Sheets

Specification includes a Sequence Listing.

OLIGOPEPTIDE WITH LIPID-LOWERING ACTIVITY, PREPARATION METHOD AND APPLICATION THEREOF

TECHNICAL FIELD

The disclosure relates to the field of biotechnologies, and more particularly to an oligopeptide with lipid-lowering activity, a preparation method and an application thereof.

STATEMENT REGARDING SEQUENCE LISTING

The sequence listing associated with this application is provided in text format in lieu of a paper copy and is hereby incorporated by reference into the specification. The name of the XML file containing the sequence listing is 23062THXT-USP1-SL.xml. The XML file is 1,765 bytes; is created on Aug. 29, 2023; and is being submitted electronically via EFS-Web.

BACKGROUND

Obesity is a metabolic disease caused by excessive energy intake or changes in body metabolism, resulting in the accumulation of body fat, especially triglycerides, accompanied by the occurrence of type II diabetes, nonalcoholic fatty liver disease, cardiovascular disease and other diseases, which jeopardize more than ⅓ of the world's population. For a long time, people are enthusiastic about finding drugs to treat or prevent obesity, such as orlistat, sibutramine, metformin, and statins, but clinical use is still accompanied by a variety of side effects. With the development of medicine and biotechnology, polypeptide and protein drugs have been emerging continuously, which have many advantages such as such as high efficacy, easy metabolism, low accumulation, low toxicity, and small side effects. Therefore, the development of polypeptide and protein drugs has become a research hotspot.

In the related art, there is a lack of oligopeptides with natural sources, high efficiency, safety and lipid-lowering activity.

SUMMARY

Purposes of the disclosure are to provide an oligopeptide with lipid-lowering activity, derived from loach protein, which is characterized by high safety, high efficiency, and wide source.

A purpose of the disclosure is to provide a preparation method for the aforementioned oligopeptide, which is simple, safe, efficient, and has good repeatability.

Another purpose of the disclosure is to provide an application of the oligopeptide in preparation of a drug, a cosmetic, or a functional food with lipid-lowering activity.

The purposes of the disclosure are achieved through the following technical solutions.

Specifically, an oligopeptide with lipid-lowering activity is provided, the amino acid sequence of the oligopeptide is as shown in SEQ ID NO: 1.

The disclosure also provides a preparation method for the oligopeptide, which includes the following steps: (1) hydrolyzing a loach protein with proteases to obtain an enzymatic hydrolysis product; (2) separating the enzymatic hydrolysis product using an ultrafiltration membrane, and taking a component with a molecular weight less than 3 kilodalton (kDa); and (3) filtering and separating the component with the molecular weight less than 3 kDa by Sephadex G-15 to obtain the oligopeptide.

In an embodiment of the disclosure, the proteases in the step (1) are bromelain and alkaline protease.

In an embodiment of the disclosure, the hydrolyzing a loach protein with proteases to obtain an enzymatic hydrolysis product of the step (1) includes hydrolyzing the loach protein using the bromelain and the alkaline protease sequentially.

In an embodiment of the disclosure, a hydrolysis time using the bromelain in the step (1) is in a range of 4-6 hours, and a hydrolysis time using the alkaline protease in the step (1) is in a range of 0.5-1.5 hours.

In an embodiment of the disclosure, a cutoff molecular weight of the ultrafiltration membrane in the step (2) is 3 kDa.

In an embodiment of the disclosure, in step (3), the filtering and separating the component with the molecular weight less than 3 kDa by Sephadex G-15 to obtain the oligopeptide of the step (3) includes eluting the component with the molecular weight less than 3 kDa by using deionized water with an elution flow rate of 0.8 milliliters per minute (mL/min), and taking an eluent with a retention time of 125-155 minutes to thereby obtain the oligopeptide.

The disclosure also provides an application of the oligopeptide in preparation of a drug, a cosmetic, or a functional food with lipid-lowering activity.

The disclosure also provides a drug, a cosmetic, or a functional food including the oligopeptide.

The oligopeptide of the disclosure is isolated from loach protein, and the amino acid sequence is as shown in SEQ ID NO: 1. It is found to have strong lipid-lowering activity as measured by the secretion amount of lipid droplets and the intracellular triglyceride content of sodium palmitate (PA)-induced HepG2 cells in vitro and can be applied to the preparation of medicines, cosmetic products and functional products with lipid-lowering activity, and it has a broad prospect in the field of food, medicine and cosmetic products. The oligopeptide of the disclosure is derived from the loach protein and therefore has high safety. The preparation method is simple, easy to operate, and has a wide range of sources.

BRIEF DESCRIPTION OF DRAWINGS

FIG. 1A illustrates effects of respective components on cell proliferation viability of the HepG2 cells, where a control group represents a control well, and LPH-I, LPH-II and LPH-III represent sample wells respectively added LPH-I, LPH-II or LPH-III (150 micrograms per milliliter abbreviated as μg/mL). FIG. 1B illustrates effects of respective components on secretion of lipid droplets in the HepG2 cells induced by PA, where Control represents a blank control, PA represents a well intervened by basal medium, PA/LPH-I represents a well intervened by the basal medium with 150 μg/mL LPH-I, and PA/LPH-II and PA/LPH-III are analogized in the same method as PA/LPH-I. FIG. 1C illustrates effects of respective components on lipid content of the HepG2 cells induced by PA, where the following PA and Sample represent substances added during the intervention, "+" represents that the corresponding substance is added, and "−" represents that that the corresponding substance is not added. FIG. 1D illustrates effects of respective components on content of triglyceride (TG) in the HepG2 cells induced by PA, where the following PA and Sample represent substances added during the intervention, "+" represents that the corresponding substance is added, "−" represents that that the corresponding substance is not added, and the ordinate represents the content of triglyceride in micromoles per gram of protein (μmol/gprot). In addition, ## represents a significant difference compared with the blank well (p<0.01), and ** represents a significant difference compared with the model well (p<0.01), the same below.

FIG. 3A illustrates effects of G1, G2, G3, G4, G5, G6 and G7 (100 μg/mL) on the cell proliferation viability of the HepG2 cells, where a control group represents a control well, and G1, G2, G3, G4, G5, G6 and G7 represent sample wells added with G1, G2, G3, G4, G5, G6 and G7 respectively. FIG. 3B illustrates effects of G1-G7 (100 μg/mL) on the secretion of lipid droplets in the HepG2 cells induced by PA, where Control represents a blank control, PA represents a well intervened by the basal medium, PA/G1 represents a well intervened by the basal medium supplemented with G1; and PA/G2, PA/G3, PA/G4, PA/G5, PA/G6, and PA/G7 are analogized in the same method as PA/G1. FIG. 3C illustrates effects of G1-G7 of 100 μg/mL on the secretion of lipid droplets in the HepG2 cells induced by PA, where the following PA and Sample represent substances added during the intervention, "+" represents that the corresponding substance is added, and "−" represents that that the corresponding substance is not added. FIG. 3D illustrates effects of G1-G7 (100 μm/mL) on the content of triglyceride (TG) in the HepG2 cells induced by PA, where the following PA and Sample represent substances added during the intervention, "+" represents that the corresponding substance is added, "−" represents that that the corresponding substance is not added, and the ordinate represents the triglyceride content in micromoles per gram of protein (μmol/gprot).

FIG. 5A illustrates effects of different concentrations of the oligopeptide AYPF on the cell proliferation viability of the HepG2 cells, where a control group represents a control well, and 16, 32, 64, 128, 256 and 512 represent sample wells respectively added 16 micromoles per liter (μM), 32 μM, 64 μM, 128 μM, 256 μM and 512 μM oligopeptide AYPF. FIG. 5B illustrates effects of the oligopeptide AYPF on the secretion of lipid droplets in the HepG2 cells induced by PA, where Control represents a blank control, PA represents a well intervened by the basal medium, PA/64 μM AYPF represents a well intervened by the basal medium supplemented with 64 μM AYPF; and PA/128 μM AYPF represents a well intervened by the basal medium supplemented with 128 μM AYPF. FIG. 5C illustrates effects of different concentrations of the oligopeptide AYPF on the secretion of lipid droplets in the HepG2 cells induced by PA, where the following PA and AYPF represent substances added during the intervention, "+" represents that the corresponding substance is added, and "−" represents that that the corresponding substance is not added. FIG. 5D illustrates effects of different concentrations of the oligopeptide AYPF on the content of triglyceride (TG) in the HepG2 cells induced by PA, where the following PA and AYPF represent substances added during the intervention, "+" represents that the corresponding substance is added, "−" represents that that the corresponding substance is not added, and the ordinate represents the content of triglyceride in micromoles per gram of protein (μmol/gprot).

DETAILED DESCRIPTION OF EMBODIMENTS

Figure 1A:
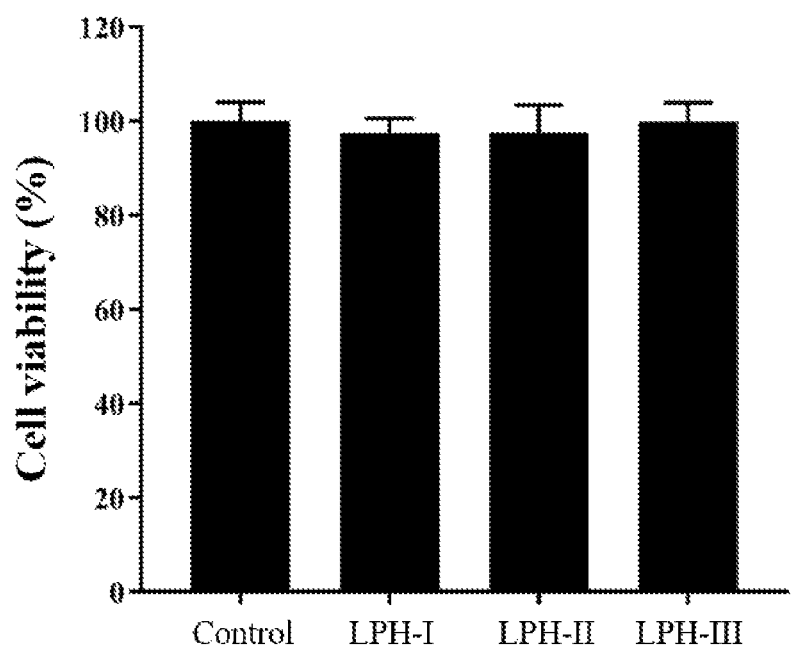
FIGS. 1A-1D illustrate effects of ultrafiltration components on lipid accumulation in HepG2 cells induced by sodium palmitate (PA). Specifically.

Experimental methods used in the following embodiments are all conventional unless otherwise specified.

Materials and reagents used in the following embodiments can be obtained from commercial sources unless otherwise specified.

1. Materials: bromelain (300 units per milligram abbreviated as U/mg), from Shanghai yuanye Bio-Technology Co., Ltd.; alkaline protease (200 U/mg), from Shanghai yuanye Bio-Technology Co., Ltd.; ultrafiltration membranes (10 kilodalton abbreviated as kDa, 3 kDa), from MilliporeSigma, USA; Sephadex G-15, China Health Group; HepG2 cell line, from cell bank of Shanghai, Chinese Academy of Sciences; fetal bovine serum (FBS), high glucose Dulbecco's Modified Eagle Medium (DMEM), Penicillin-Streptomycin (100×), trypsin ethylenediaminetetraacetic acid (EDTA) (0.05%), PBS phosphate buffer (1×, pH 7.2), from Gibco™ Thermo Fisher Scientific Inc., USA; dimethyl sulfoxide (DMSO), from Sigma Corporation, USA; Oil red O dye, from Shanghai yuanye Bio-Technology Co., Ltd.; sodium palmitate (PA, specification: 99%), from Shanghai Macklin Biochemical Co., Ltd.; bovine serum albumin (BSA), from Sigma Corporation, USA; bicinchoninic acid (BCA) protein concentration determination kit, from Beyotime Biotechnology Co., Ltd.; tissue cell triglyceride assay kit E1013, from Beijing Applygen Technologies Inc. Other reagents are analytically pure in China.

2. Main instruments and equipment: biosafety cabinet, from Thermo Fisher Scientific Inc.; MZE multi-function microplate reader, from Molecular Devices, LLC., USA; SL 16R desktop centrifuge, from Thermo Fisher Scientific Inc.; carbon dioxide ($CO_2$) incubator, from Thermo Fisher Scientific Inc.; inverted fluorescent microscope, from Carl Zeiss Vision Inc, Germany.

Embodiment 1 Preparation of an Oligopeptide with Lipid-Lowering Activity (1) Pretreatment of loach (*Misgurnus anguillicaudatus*): before the experiment, the loach is fed in clean water for one week and vomited. Then, the loach is slaughtered, and the head, tail, viscera and blood are removed. The meat is collected and stirred twice in a meat grinder. The obtained meat paste is placed in a polyethylene bag and frozen at 20° C. for later use.

(2) Enzymatic hydrolysis of loach protein: 100 grams (g) of meat paste of the loach are weighed and 200 milliliters (mL) of deionized water are added, and stirred evenly to obtain turbid solution with pH value of 6.5. There is no need to adjust the pH, then 1 mL of aqueous solution containing 300 mg bromelain (300 U/mg, Shanghai yuanye Bio-Technology Co., Ltd., CAS No.: 37189-34-7) is added in the turbid solution, enzymatic hydrolysis is performed at 55° C. for 5 hours, and the enzyme is inactivated in a boiling water bath for 10 minutes. Then, the pH value is adjusted to 8.0 with 0.1 mole per liter (M) aqueous sodium hydroxide solution, and 1 mL aqueous solution containing 450 milligrams (mg) alkaline protease (200 U/mg, Shanghai yuanye Bio-Technology Co., Ltd., CAS No.: 9014-01-1) is added for enzymatic hydrolysis at 50° C. for 1 hour, and the enzyme is inactivated in a boiling water bath for 10 minutes. The solution after enzymatic hydrolysis is cooled to room temperature, centrifuged at 5000 revolutions per minute (r/min) for 20 minutes, supernatant is collected, dialyzed and desalted, and vacuum freeze-dried to obtain a loach protein hydrolysate (LPH).

(3) Ultrafiltration of the loach protein hydrolysate: ultrafiltration membranes with cutoff molecular weights of 10 kDa and 3 kDa are selected. Using deionized water, the loach protein hydrolysate is prepared into a solution with a mass concentration of 1%, and the insoluble substances are removed by filtration using a cellulose membrane with a pore size of 0.45 micrometers (μm). Then, the solution is separated by a small tangential flow ultrafiltration system of Labscale, an ultrafiltration membrane with a cutoff molecular weight of 10 kDa is firstly selected for separation to obtain a component with a molecular weight greater than 10 kDa (denoted as component LPH-I) and a component with a molecular weight less than or equal to 10 kDa; then, the component with the molecular weight less than or equal to 10 kDa is separated by an ultrafiltration membrane with a cutoff molecular weight of 3 kDa to obtain a component with a molecular weight greater than or equal to 3 kDa and less than or equal to 10 kDa (denoted as component LPH-II) and a component with a molecular weight less than 3 kDa (denoted as component LPH-III). During ultrafiltration, the pressure of the pump is adjusted to 0.2 MPa and the ultrafiltration temperature is 4° C.

After ultrafiltration, the components with different molecular weights, LPH-I (>10 kDa), LPH-II (3-10 kDa) and LPH-III (<3 kDa), are desalted and freeze-dried, and the effects of respective components on the cell proliferation viability of normal HepG2 cells are detected by 3-(4,5-dimethylthiazol-2-yl)-2,5-diphenyltetrazolium bromide (MTT) assay. In addition, the effects of LPH-I (>10 kDa), LPH-II (3-10 kDa) and LPH-III (<3 kDa) on lipid accumulation (lipid droplet secretion and intracellular triglyceride (TG) content) in HepG2 cells induced by sodium palmitate (PA) are detected to evaluate the lipid-lowering activity of the oligopeptide.

i) MTT (also referred to as thiazole blue) assay is used to detect the effects of various components (LPH-I, LPH-II and LPH-III) on the cell proliferation viability of normal HepG2 cells: HepG2 cells in logarithmic growth period are taken and prepared into a cell suspension of $4 \times 10^5$ cells/mL with the high glucose DMEM medium containing 10% FBS. Sample wells are set in a 96-well plate, and 100 μL of cell suspension is added to each sample well, and the cells are cultured in a cell incubator for 24 hours to adhere to the wall. After removing the culture medium from the sample wells, the components LPH-I (>10 kDa), LPH-II (3-10 kDa) and LPH-III (<3 kDa) are respectively dissolved in the high glucose DMEM culture medium containing 10% FBS to prepare an oligopeptide culture medium with a concentration of 150 μg/mL, and then added to each sample well, with a volume of 100 μL per well. A blank well is set, no cells are present compared with the sample wells, and 100 μL PBS phosphate buffer (1×, pH 7.2) is used to replace the oligopeptide culture medium. A control well is set with cells compared with the sample wells, and 100 μL PBS phosphate buffer (1×, pH 7.2) is used to replace the oligopeptide culture medium. After the 96-well plate is incubated in an incubator at 37° C. for 24 hours, 10 μL of MTT solution (5 mg/mL) is added to each well, after incubation for 4 hours, the solution in the 96-well plate is removed, 150 μL of DMSO is added to each well, and the plate is oscillated in a constant temperature oscillation box at 37° C. for 20 minutes. The absorbance is measured at 570 nanometers (nm) wavelength in a microplate reader.

Cell proliferation viability=$(OD_{sample\ well} - OD_{blank\ well})/(OD_{control\ well} - OD_{blank\ well}) \times 100\%$.

Results as shown in FIG. 1A, after the components are treated for 24 hours, there is no significant difference in absorbance, indicating that different components of LPH-I (>10 kDa), LPH-II (3-10 kDa) and LPH-III (<3 kDa) have no effect on the viability of HepG2 cells, which suggests that the safety of the components of LPH-I (>10 kDa), LPH-II (3-10 kDa) and LPH-III (<3 kDa) is great.

ii) Oil red O staining: HepG2 cells in logarithmic growth period are taken and inoculated into a 24-well plate with $5 \times 10^4$ cells/well, and 500 μL of the high glucose DMEM medium containing 10% FBS is added to each well for culture. After the cells are grew to 90% fusion degree, the medium is removed, 500 μL FBS-free high glucose DMEM culture medium is added to each well to starve for 16 hours. After that, 500 μL of fresh high glucose DMEM medium containing 150 μM PA and 1% BSA (denoted as basal medium), 150 μg/mL of LPH-I medium, 150 μg/mL of LPH-II medium and 150 μg/mL of LPH-III medium are added to each well, and four parallel wells are set in each group and induced for 24 hours. Cells cultured in the high glucose DMEM medium containing 1% BSA is used as a blank control. After the end of induction, the supernatant is absorbed and discarded, the plate is carefully rinsed with PBS phosphate buffer solution for 3 times, fixed with 10% neutral formalin solution for 30 minutes, rinsed with PBS phosphate buffer solution for 3 minutes each time, slightly dried, differentiated with 60% isopropanol aqueous solution, added with a staining solution containing oil red O dye (obtained by adding 0.3 g oil red 0 dye to 100 mL of 60% isopropyl alcohol aqueous solution), and shaken on a shaker at 37° C. in the darker. The staining solution is discarded, the cells are differentiated with 60% isopropanol aqueous solution until the background is clear, and then rinsed with PBS phosphate buffer solution for three times, and then put under Lycra inverted microscope (200×) for photo analysis.

After photographing, 200 uL isopropanol is added to each well, and the oil red O dye is re-solubilized on a shaker at 37° C., and its absorbance at 510 nm is measured. Taking the lipid content of the blank control as 100%, the percentage of lipid content of respective components after oligopeptide treatment relative to the blank control is calculated, so as to determine the in vitro lipid-lowering effect of the loach polypeptide.

Figure 1B:
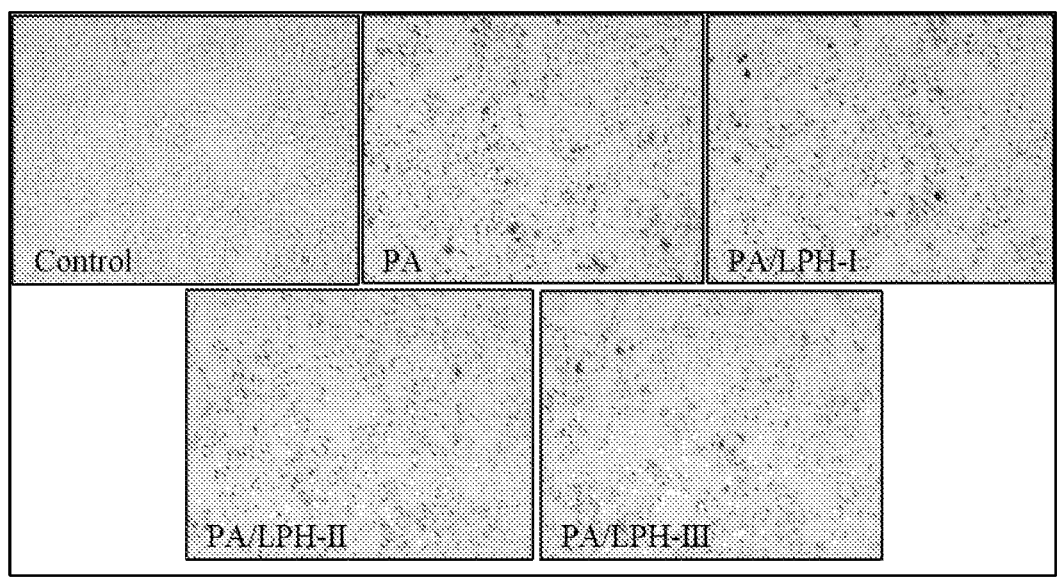
Figure 1C:
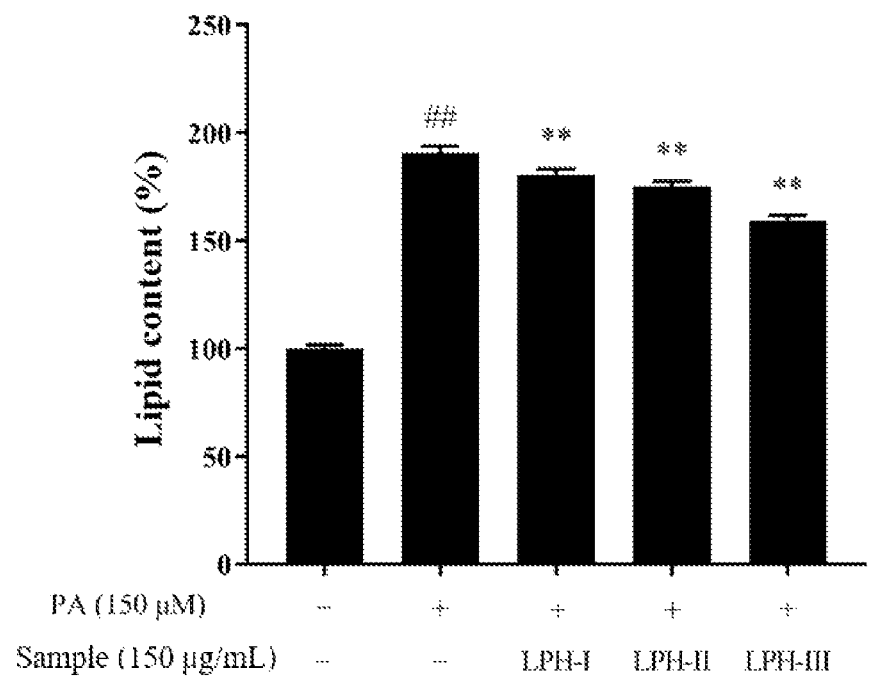

Results as shown in FIGS. 1B-1C, it is observed by oil red O staining that the cell morphology of the blank control group is clear, and the number of red droplets is very small, while the number and volume of lipid droplets of the cells are significantly increased after PA stimulation. Compared with the model (PA) group, the number of red droplets in the groups with LPH-I, LPH-II and LPH-III components are significantly decreased. After re-solubilizing the oil red O dye, the absorbance at 510 nm is measured. It is found that the lipid droplets secretion of cells could be significantly reduced by adding LPH-I, LPH-II and LPH-III components.

iii) Determination of triglyceride (TG) content of cells: HepG2 cells in logarithmic growth period are taken and inoculated into a 24-well plate with $5 \times 10^4$ cells/well, and 500 μL of high glucose DMEM medium containing 10% FBS is added to each well for culture. After the cells are grew to 90% fusion degree, the culture medium is removed, 500 μL FBS-free high glucose DMEM culture medium is added to each well to starve for 16 hours. After that, 500 μL of fresh high glucose DMEM medium containing 150 μM PA and 1% BSA (denoted as basal medium), 150 μg/mL of LPH-I medium, 150 μg/mL of LPH-II medium and 150 μg/mL of LPH-III medium are added to each well, and four parallel wells are set in each group and induced for 24 hours. Cells cultured in the high glucose DMEM medium containing 1% BSA is used as a blank control. After the end of induction, the cells are rinsed with precooled PBS buffer for three times, then lysed on ice with lysis solution for 15 minutes, and then collected into an EP tube with a cell scraper and centrifuged at 12,000 rpm for 15 min at 4° C., and then the supernatant is used to determine the triglyceride content of cells by using tissue cell triglyceride assay kit E1013.

Figure 1D:
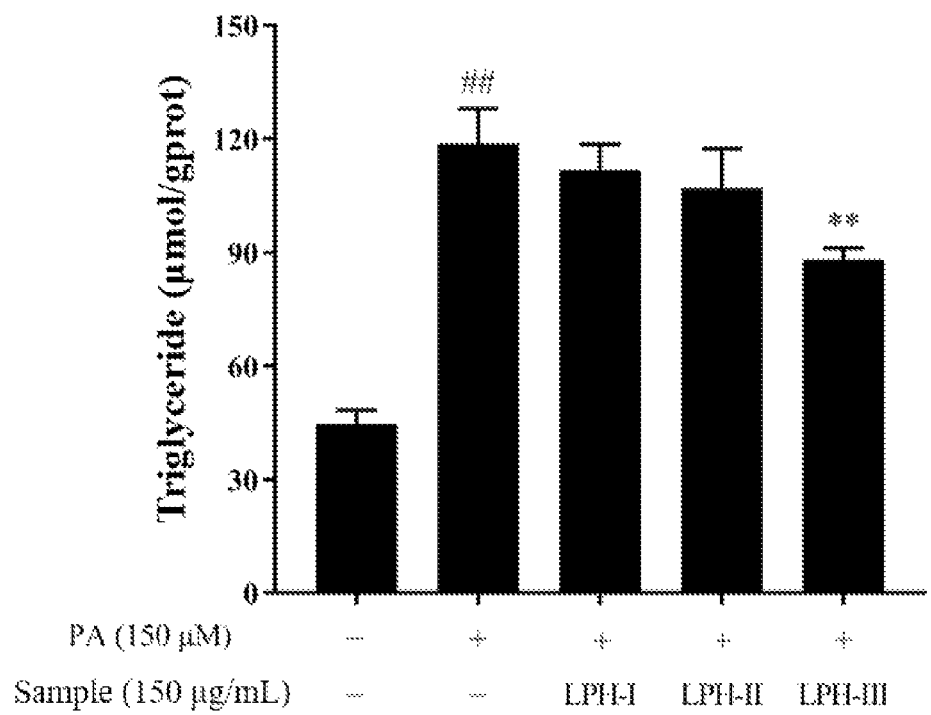

Results as shown in FIG. 1D, the intracellular triglyceride content is significantly increased after PA stimulation compared with that of the control group, which is alleviated after adding LPH-I, LPH-II and LPH-III components, with the LPH-III component having the best alleviating effect.

The above experimental results show that after ultrafiltration separation, the LPH-I, LPH-II and LPH-III components all have certain lipid-lowering effects in vitro, among which LPH-III has the best lipid-lowering effect. Therefore, the LPH-III component is freeze-dried and separated by gel filtration, so as to obtain more precise lipid-lowering components.

(4) Gel filtration separation: the model of the sephadex (also referred to as glucose gel) filler is Sephadex G-15. A size of chromatographic column is 1.6×75 cm. Firstly, a certain amount of gel filler is prepared according to the volume of the chromatographic column and the required gel volume, the dry gel is soaked in the eluent or deionized water for a period of time, after which it can be boiled for 5-10 minutes to make it fully dissolved, and then the filler is loaded into the column, taking care not to have any faults or big bubbles, and the height of loading is about 65 cm (which can be adjusted according to the specifications of the chromatographic column).

A gel column, a constant fluid pump, an ultraviolet detection system and an automatic collector are connected in a specific order. The constant fluid pump is adjusted to the flow rate of 0.8 mL/min, and balanced elution is carried out with deionized water (Removing air bubbles from the system and pressing the filler to stabilize it). The freeze-dried sample of LPH-III component is re-dissolved in deionized water to prepare a sample with a concentration of 30 mg/mL, and filtered with a 0.45 μm aqueous filter membrane to remove insoluble impurities. 8 mL of the filtered sample (LPH-III component with a concentration of 30 mg/mL) is taken and loaded onto the column, and eluted with deionized water at an elution rate of 0.8 mL/min. The eluent is collected, 4 mL per tube, with ultraviolet detection wavelength at 220 nm.

Figure 2:
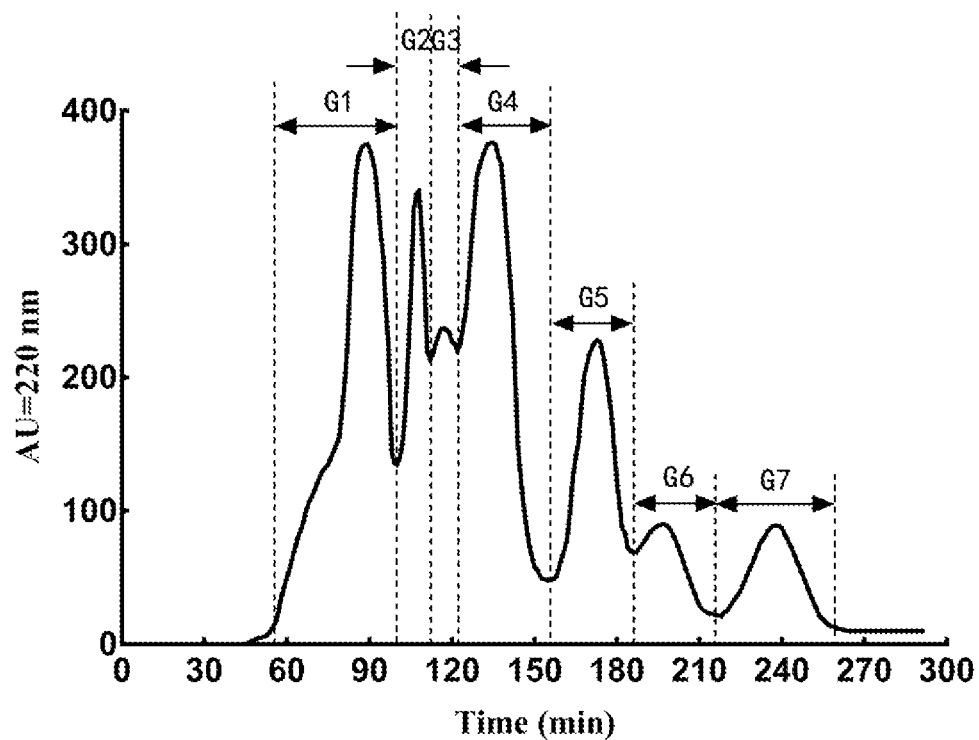
FIG. 2 illustrates a chromatogram of LPH-III separated by Sephadex G-15 gel filtration, where the abscissa is retention time (minutes abbreviated as min) and the ordinate is signal response value (millivolt abbreviated as mV) at 220 nanometers (nm).

As shown in FIG. 2, the LPH-III component is separated by Sephadex G-15 gel filtration and divided into seven peak components, which are named G1, G2, G3, G4, G5, G6 and G7.

The peak components are combined, concentrated by suspension distillation, and then freeze-dried, and the effects of G1-G7 with the concentration of 100 μg/mL on the proliferation viability of the HepG2 cells are determined by the method of i) described in this embodiment. The in vitro lipid-lowering effects of 100 μg/mL G1-G7 are determined by the methods in ii) and iii) described in this embodiment, and the component with the highest activity is used for peptide sequence analysis.

Figure 3A:
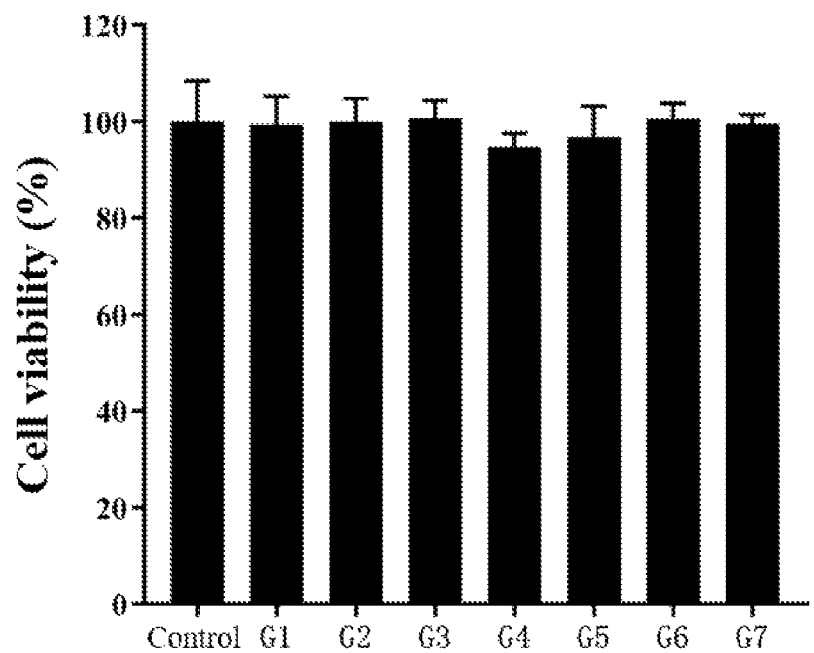
FIGS. 3A-3D illustrate effects of gel filtration separated components on the lipid accumulation in the HepG2 cells induced by PA. Specifically.
Figure 3B:
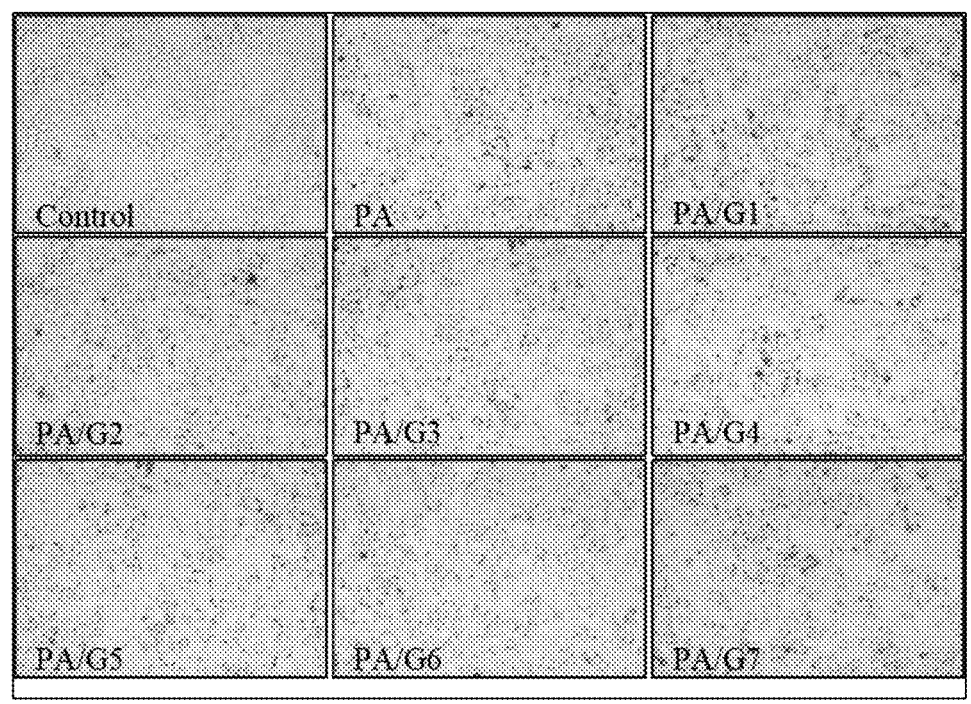
Figure 3C:
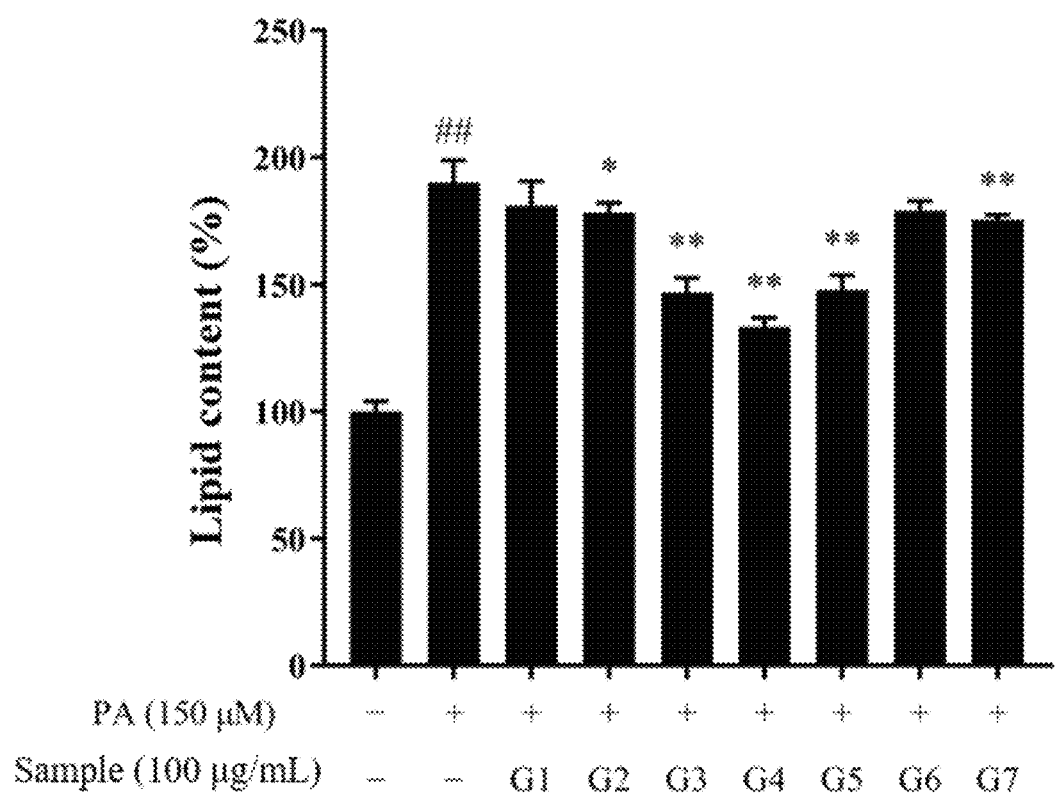
Figure 3D:
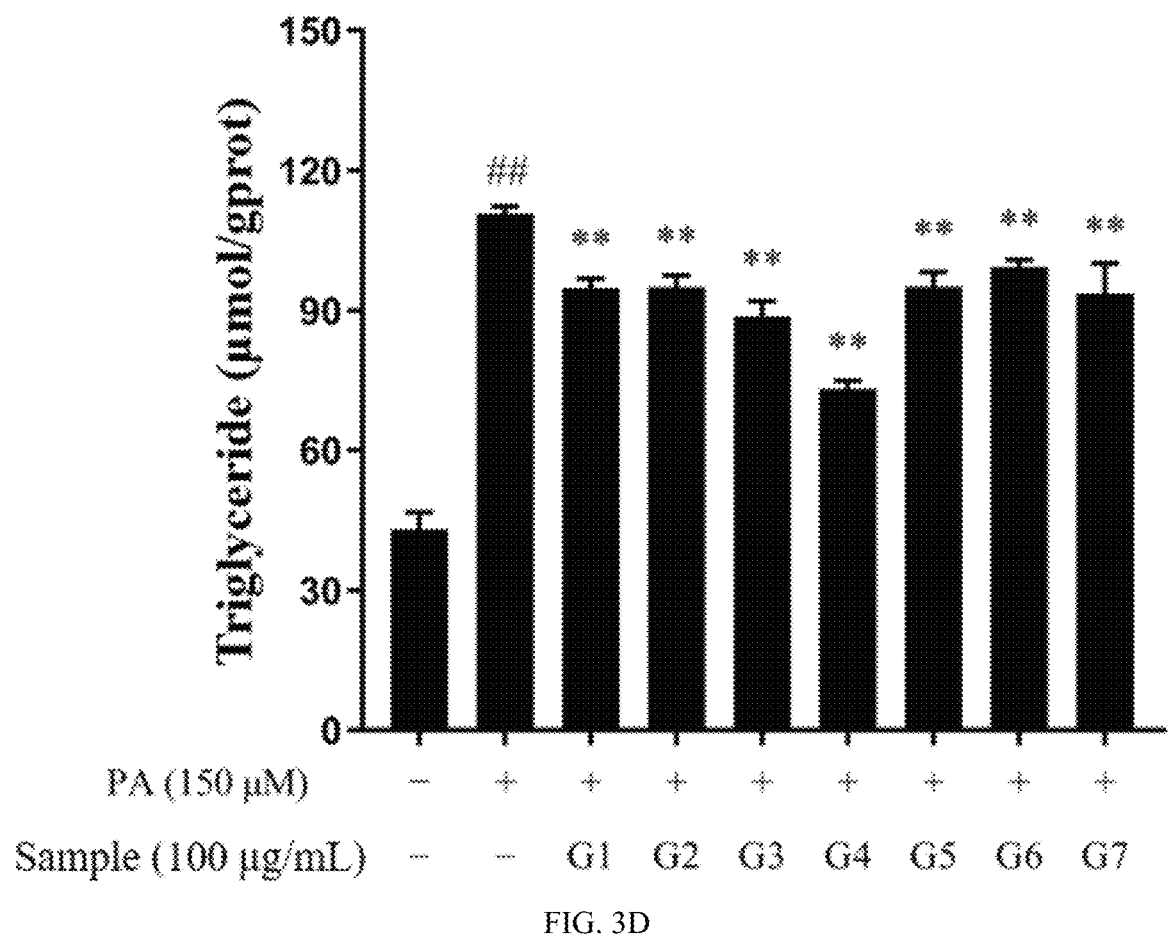

As shown in FIGS. 3A-3D, G1, G2, G3, G4, G5, G6 and G7 have no effect on the proliferation activity of the HepG2 cells at the concentration of 100 μg/mL (see FIG. 3A), and can significantly reduce the increase of lipid droplet secretion induced by PA (see FIGS. 3B-3C) to alleviate the intracellular triglyceride content (see FIG. 3D). Among them, G4 peak component (corresponding retention time is 125-155 minutes) has the best lipid-lowering effect in vitro. Therefore, the amino acid sequence of G4 peak component is analyzed.

Figure 4:
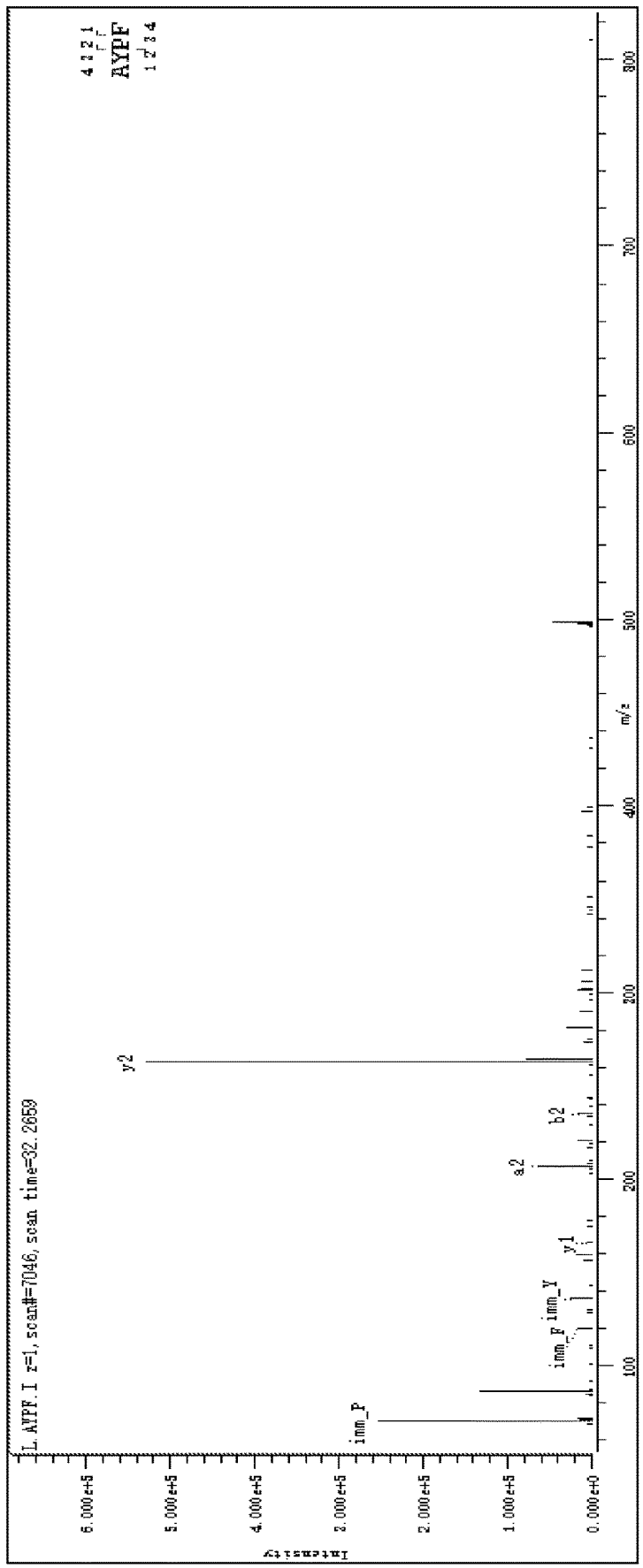
FIG. 4 illustrates a secondary mass spectrum of oligopeptide AYPF, where the abscissa represents a mass-to-charge ratio (m/z) value of ions, and the ordinate represents the intensity of ion current.

(5) Structural identification: LC-MS/MS is used to detect the purity and amino acid sequence of an active component in G4 peak. The G4 peak component is freeze-dried to obtain freeze-dried powder of the G4 peak component. The freeze-dried powder of the G4 peak component is dissolved in deionized water to prepare a protein solution with a concentration of 20 μg/mL. Mobile phase A is 0.1% formic acid aqueous solution, and mobile phase B is 0.1% formic acid acetonitrile solution. BEH C18 chromatographic column is selected. The elution procedure is: from 0 to 5 minutes, while the mobile phase A is decreased linearly from 100% to 85%, the mobile phase B is increased linearly from 0% to 15%; and from 5 to 10 min, the mobile phase A is increased linearly from 85% to 100%, while the mobile phase B is decreased linearly from 15% to 0%. The percentage in the elution procedure is the volume percentage concentration. After the sample passes through the liquid chromatography separation system, the peptide fragments are broken into fragments with different molecular weights by the mass spectrometry system, and the ion fragments are separated by mass number by the mass analyzer and detected by the detector to obtain the mass spectrogram, as shown in FIG. 4. By analyzing the mass spectrum, it is found that the active component in the G4 peak is an oligopeptide with the amino acid sequence of AYPF, with a molecular weight of 496.56 Da and a mass percentage greater than or equal to 98%.

Embodiment 2 Lipid-Lowering Activity of the Oligopeptide AYPF

Figure 5A:
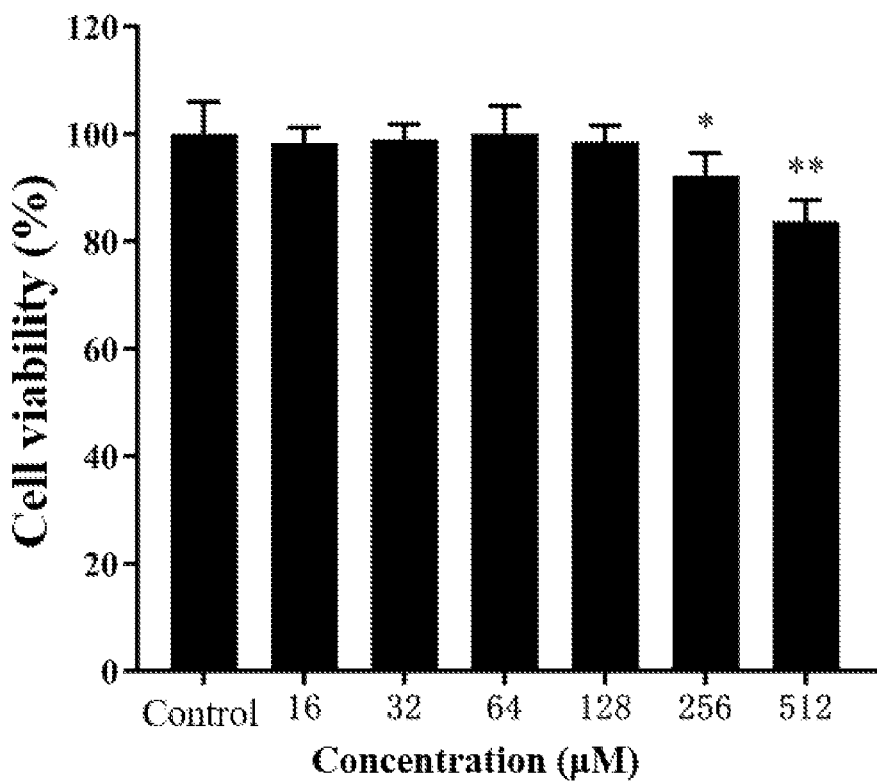
FIGS. 5A-5D illustrate effects of the oligopeptide AYPF on the lipid accumulation in the HepG2 cells induced by PA. Specifically.

An oligopeptide, AYPF (as shown in SEQ ID NO:1), is synthesized by Genescript Biotechnology Co., Ltd. by using FlexPeptide™ polypeptide synthesis technology. The effects of the oligopeptide AYPF at concentrations of 16 μM, 32 μM, 64 μM, 128 μM, 256 μM and 512 μM on the proliferation activity of the HepG2 cells are determined by the method of i) described in the embodiment 1. Results as shown in FIG. 5A, when the concentration is 256 μM, the oligopeptide has a certain effect on the cell viability. Therefore, 64 μM and 128 μM are used as the research concentrations to carry out the follow-up experiments.

Figure 5B:
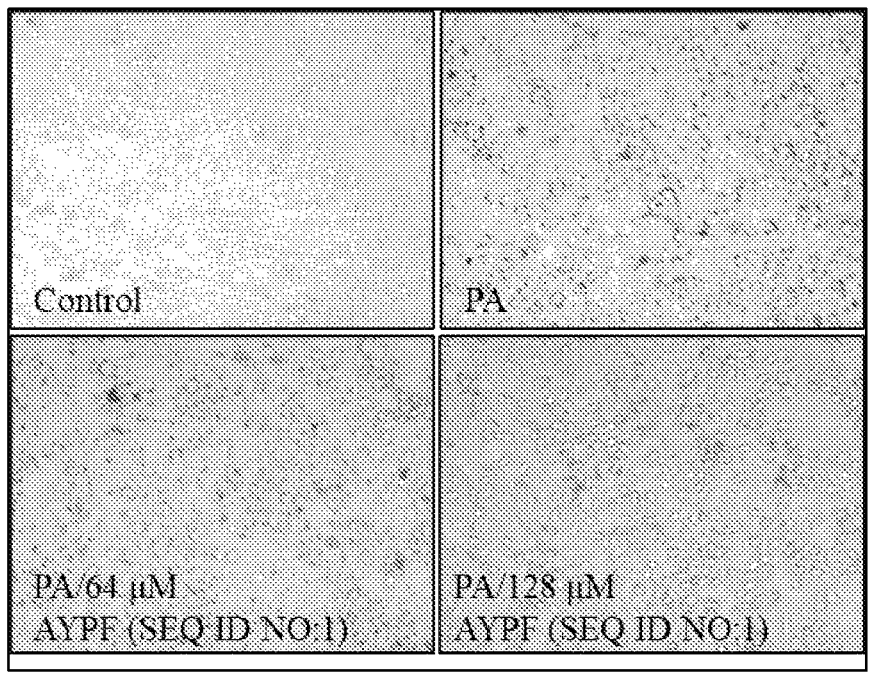
Figure 5C:
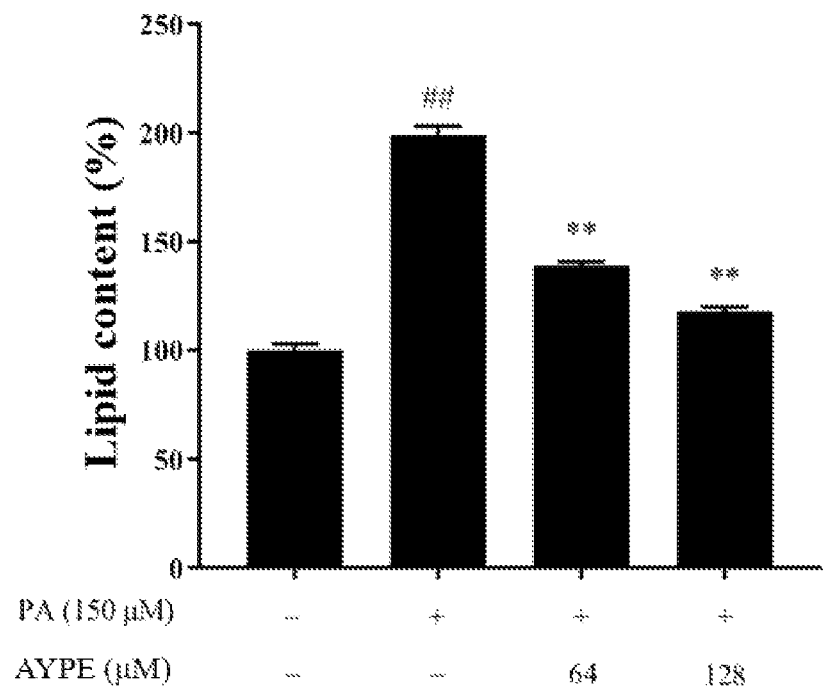
Figure 5D:
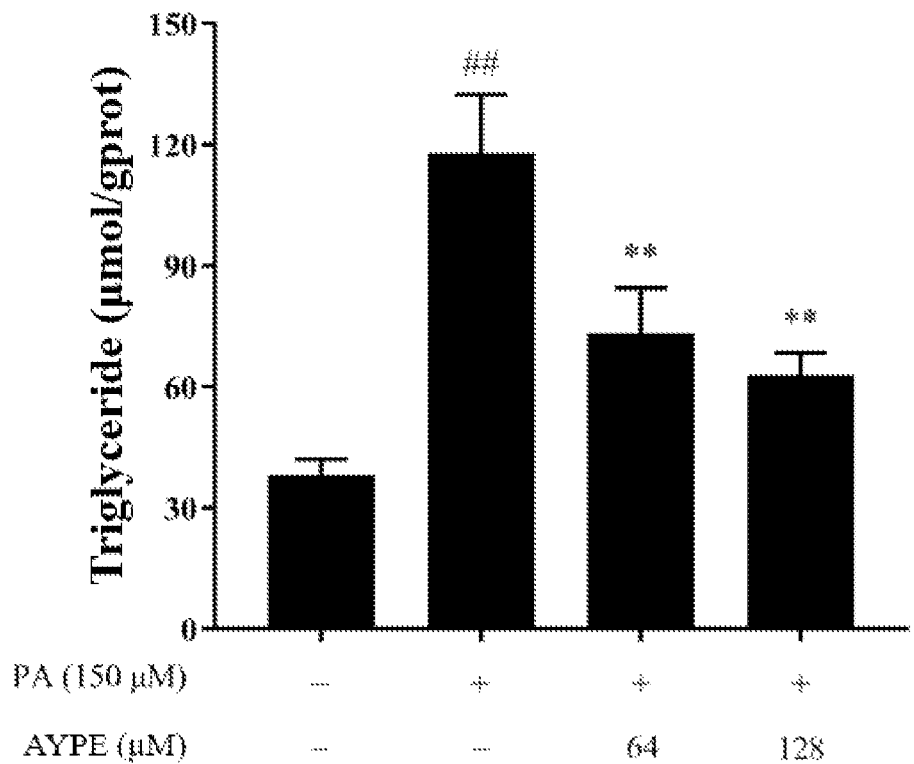

The in vitro lipid-lowering effects of the oligopeptide AYPF at concentrations of 64 μM and 128 μM are determined by the methods ii) and iii) described in the embodiment 1. The results show that the oligopeptide AYPF could significantly reduce the increase of lipid droplet secretion induced by PA (see FIG. 5B-5C). The lipid content in the HepG2 cells induced by PA reaches 198.89±3.37% (calculated as 100% of the blank control), and the lipid contents in the cells are only 138.91±1.54% and 117.84±1.60% when the oligopeptides AYPF of 64 μM and 128 μM are used. It can be seen from FIG. 5D that the triglyceride content in the normal HepG2 cells is 38.04±3.18 μmol/gprot, and that in the HepG2 cells induced by PA is 117.89±11.78 μmol/gprot. Under the intervention of 64 μM and 128 μM oligopeptides AYPF, the contents of triglyceride in the cells are only 73.25±7.12 μmol/gprot and 62.83±4.51 μmol/gprot, which indicates that the oligopeptide AYPF could significantly alleviate the increase of intracellular triglyceride content in a dose-dependent manner, and it could be considered that the oligopeptide has a good lipid-lowering effect in vitro.

To sum up, the oligopeptide AYPF of the disclosure has good lipid-lowering activity, can significantly alleviate the lipid accumulation of the HepG2 cells induced by PA, and reduce the intracellular triglyceride (TG) content, and can be applied to the preparation of drugs, cosmetics or functional products with lipid-lowering activity.

SEQUENCE LISTING

```
Sequence total quantity: 1
SEQ ID NO: 1            moltype = AA   length = 4
FEATURE                 Location/Qualifiers
source                  1..4
                        mol_type = protein
                        organism = synthetic construct
SEQUENCE: 1
AYPF                                                                   4
```

What is claimed is:

1. A preparation method of an oligopeptide with lipid-lowering activity, comprising:

step (1), hydrolyzing a loach protein with proteases to obtain an enzymatic hydrolysis product;

step (2), separating the enzymatic hydrolysis product using an ultrafiltration membrane, and taking a component with a molecular weight less than 3 kilodalton (kDa); and step (3), eluting the component with the molecular weight less than 3 kDa by using deionized water with an elution flow rate of 0.8 milliliters per minute (mL/min) by Sephadex G-15, and taking an eluent with a retention time of 125-155 minutes to thereby obtain the oligopeptide;

wherein in the step (1), the loach protein is hydrolyzed using the bromelain and the alkaline protease sequentially;

wherein a hydrolysis time using the bromelain in the step (1) is in a range of 4-6 hours, and a hydrolysis time using the alkaline protease in the step (1) is in a range of 0.5-1.5 hours; and wherein the amino acid sequence of the oligopeptide with lipid-lowering activity is SEQ ID NO: 1.

2. The preparation method as claimed in claim 1, wherein a cutoff molecular weight of the ultrafiltration membrane in the step (2) is 3 kDa.

* * * * *